United States Patent
Randström

[11] Patent Number: 5,888,233
[45] Date of Patent: Mar. 30, 1999

[54] ARRANGEMENT FOR LEG PROSTHESIS

[75] Inventor: Bengt Randström, Järfälla, Sweden

[73] Assignee: Centri AB, Jarfalla, Sweden

[21] Appl. No.: 942,364

[22] Filed: Oct. 2, 1997

Related U.S. Application Data

[63] Continuation of PCT/SE97/00612 Apr. 11, 1997.

[30] Foreign Application Priority Data

Apr. 26, 1996 [SE] Sweden .................. 9601607

[51] Int. Cl.$^6$ .................. A61F 2/62
[52] U.S. Cl. .................. 623/38
[58] Field of Search .................. 623/38, 27, 57

[56] References Cited

U.S. PATENT DOCUMENTS

| | | |
|---|---|---|
| 3,659,294 | 5/1972 | Glabiszewski . |
| 4,969,911 | 11/1990 | Greene . |
| 5,047,063 | 9/1991 | Chen . |
| 5,425,782 | 6/1995 | Phillips .................. 623/38 |
| 5,529,576 | 6/1996 | Lundt et al. . |
| 5,746,773 | 5/1998 | Littig .................. 623/35 |
| 5,759,206 | 6/1998 | Bassett .................. 623/27 |

FOREIGN PATENT DOCUMENTS

| | | |
|---|---|---|
| 2410998 | 7/1979 | France . |
| 3937379 | 5/1991 | Germany . |
| 8-89519 | 4/1996 | Japan .................. 623/38 |
| 360257 | 9/1973 | Sweden . |
| 454046 | 11/1987 | Sweden . |
| 2 089 216 | 6/1982 | United Kingdom .................. 623/39 |
| 2 274 398 | 7/1994 | United Kingdom .................. 623/38 |

*Primary Examiner*—David H. Willse
*Attorney, Agent, or Firm*—Young & Thompson

[57] ABSTRACT

An adjustment head is provided to attach an elongated member of an artificial leg to a prosthetic leg. The adjustment head includes an upper portion and a lower portion. The upper portion provides adjustment of the elongated member in a translatory direction. The lower portion, in combination with the upper portion, provides adjustment of the elongated member in an angular direction. In making the translatory adjustment, the screw provided for this purpose will not be subject to direct breaking forces by being angled due to any angular adjustment of the elongated member, such screw always being maintained in a fixed vertical alignment.

7 Claims, 3 Drawing Sheets

ARRANGEMENT FOR LEG PROSTHESIS

This is a continuation of copending international application PCT/SE97/00612 filed 11 Apr. 1997, which designates the United States.

TECHNICAL FIELD

The present invention relates to a prosthetic device and more exactly to an improved artificial leg.

STATE OF THE ART

On the market there are to be found a number of different solutions for artificial legs. Such a device generally consists of a tube being at an upper end fixed to a sleeve to be put onto the stump of the leg, and is via a second joint coupling at an lower end fixed to a corresponding prosthetic foot device. It is important that the tube at the upper end, at the attachment to the sleeve, can be adjusted both in an angular and a translatory direction, such that the user of the artificial leg will not load the leg abnormally, which in part would result in that the motion pattern of the artificial leg will become abnormal when the patient walks, and in part that the musculature of the knee joint and the upper leg will be abnormally loaded.

Swedish Patent No. SE 454 046 discloses such a device corresponding to the one demonstrated in FIG. 1, which device via an adjustment head 11 arranged at the upper end 4 of the tube 10 by a means 16 allows setting of the angular position of the tube relative to an imagined load line. Additionally other means 12, 13 allow a translatory displacement of the tube relative to the adjustment head 11. Adjustment means 16 and 12, 13, respectively, allow a basic adjustment of the tube when having the prosthesis fitted.

Additionally a Swedish Patent No. SE 360 257 from 1970 demonstrates an adjustable connection between two members of an artificial leg or arm, or the like. This device demonstrates a square stud having the form of a cut four sided pyramid, divergently extending from the base. The device only permits an angular adjustment in two defined planes relative to the socket but no translatory adjustment of the kind achieved according to the Swedish Patent No. SE 454 046.

A French Patent FR 2 410 998 from 1977 discloses a further way of achieving an angular adjustment by means of two abutting slantingly cut plates, the mutual position of which and thereby the angle of the device may be adjusted by two small levers. The angular position is locked by tightening a through-bolt.

A demand still exists to provide an artificial leg which demonstrates both a possibility for angular adjustment in all planes relative to an imagined load line and at the same time a translatory adjustment and that the system is easily adjustable and furthermore additionally demonstrates a very good mechanical strength.

DESCRIPTION OF THE INVENTION

The present invention discloses a new combination of adjustment members for an artificial leg to achieve, in part a stable adjustment of the angular position of the tube relative to an imagined load line, and in part an adjustable setting of the translatory position of the tube relative to an upper connecting sleeve.

The object of the present invention is with a first adjustment means to set the translatory position of the tube. The first adjustment means thereby includes a supporting plate having a flat surface facing the prosthetic sleeve, whereby the flat surface abuts a lower flat surface on an upper connecting sleeve attached to the prosthetic sleeve. This connecting sleeve demonstrates a central bore permitting a through-bolt to be translatory displaced relative to the upper connecting sleeve. Furthermore a second adjustment means is used for the setting of the angular position of the tube, the adjustment means including a pyramid adapter stud integrated with the supporting plate. Additionally the pyramid adapter stud is provided with a through-hole into which the through-bolt is threaded and thereby will maintain its alignment independent of the angular position set. A number of additional adjustment means fixed into a proximal sleeve attached to the tube are used for the setting of the angular position of the tube by abutting and locking to the inclined sides of the pyramid adapter stud.

DESCRIPTION OF THE DRAWINGS

The invention will be described in form of a preferred illustrative embodiment and by means of the attached drawings in which equal reference numbers indicate equal or corresponding elements, in which.

ILLUSTRATIVE EMBODIMENTS

Figure 1:
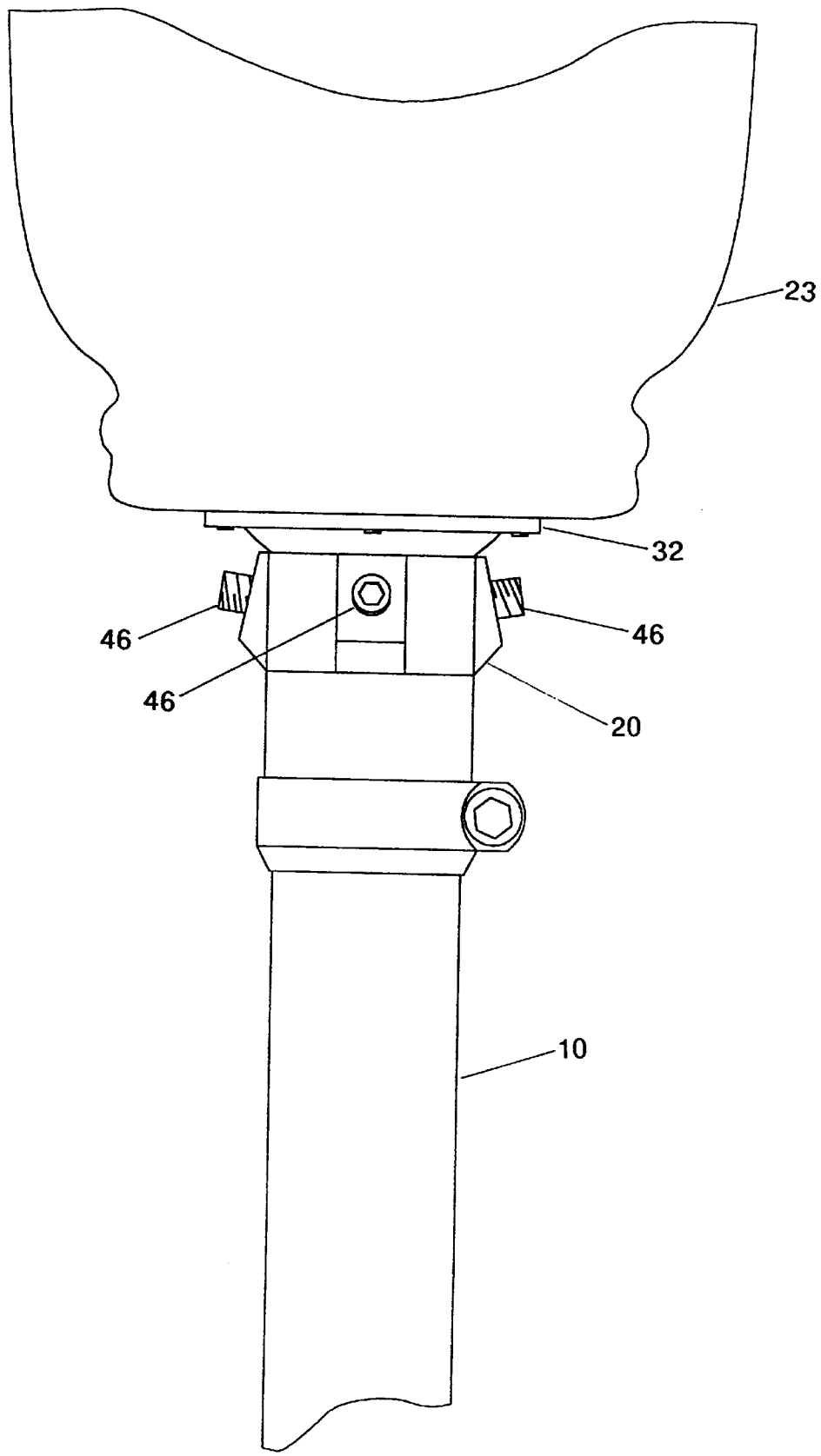
FIG. 1 demonstrates an illustrative embodiment of a portion of an artificial leg according to the present invention.
Figure 2:
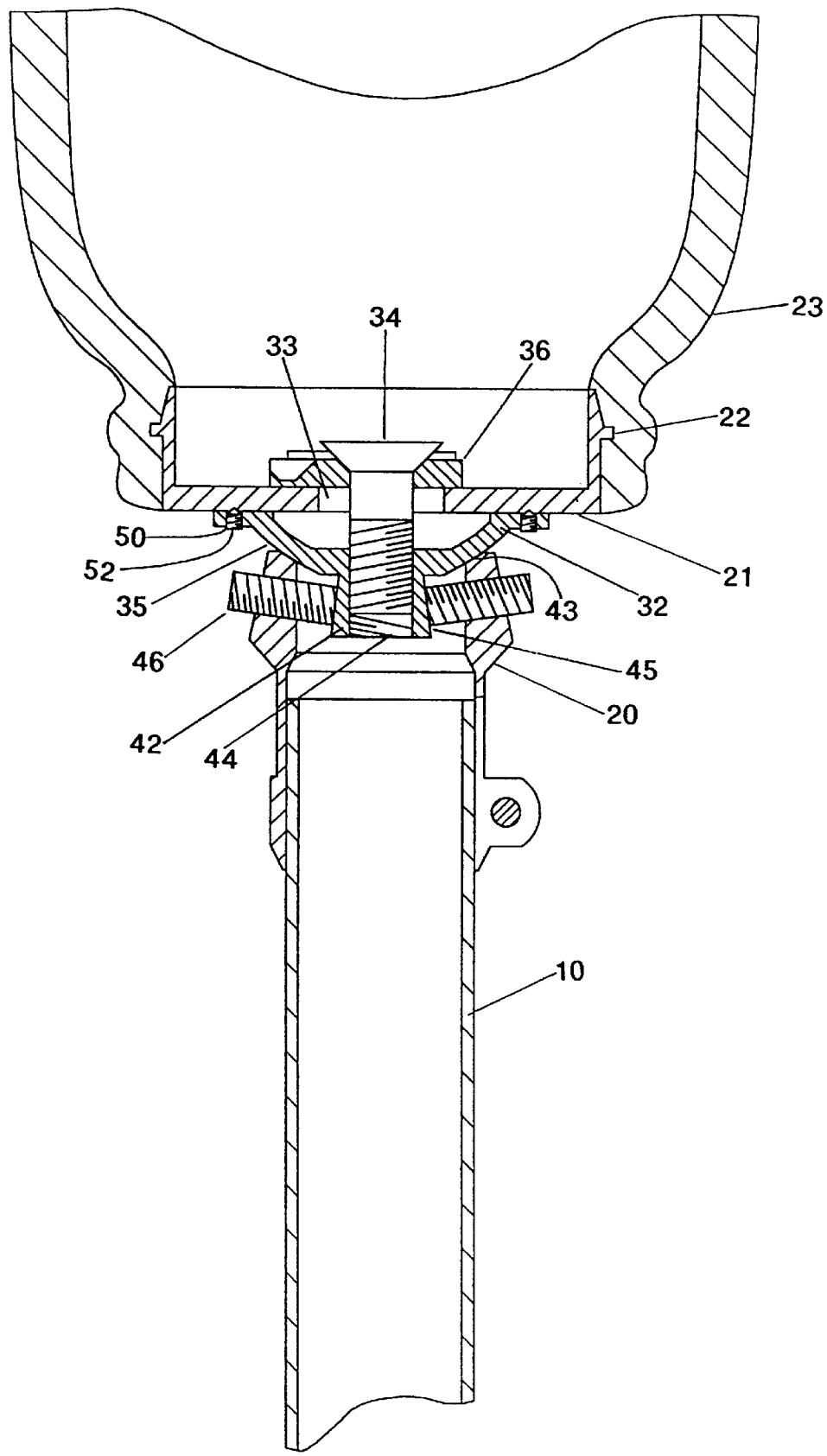
FIG. 2 demonstrates a longitudinal cross section of the embodiment of FIG. 1.

FIG. 1 demonstrates in an illustrative embodiment a portion of an artificial leg according to the present invention, while FIG. 2 demonstrates a longitudinal cross section of the device according to FIG. 1. The artificial leg device presents as main components, in a way well known to a person skilled in the art, an extension element in the form of a tube 10, an adjustment head and a prosthetic sleeve 23.

The tube 10 is, in a way well known to a person skilled in the art, fixed to a proximal sleeve 20 which thereby will constitute a lower portion of the adjustment head. The proximal sleeve is additionally provided with a number of radial threaded screws 46, for instance of a socket head cap screw type. The screws 46 incline slightly downwards in a direction towards the central line of the tube to abut a corresponding number of flat surfaces 45 of a second upper portion of the adjustment head. This upper portion constitutes a member 42 having the form of a pyramid adapter stud. In the illustrative embodiment this pyramid adapter stud has four inwardly inclined sides 45, but the pyramid adapter stud in an additional embodiment may be made having, for instance, 3 or 5 inclined sides, which will then correspond to a corresponding number of screws 46 in the lower proximal sleeve. The inclined sides of the pyramid adapter stud correspond generally to the inclination of the screws 46 in the lower proximal sleeve 20, such that the screws will approximately perpendicularly abut the inclined sides of the pyramid adapter stud. The second upper portion of the adjustment head including the member 42 further consists of a supporting plate 32 in which the pyramid adapter stud, constituting the member 42, is included as an integral portion. The supporting plate 32 presents at the sides of the pyramid adapter stud a convex surface 35 facing the proximal sleeve 20. This convex surface furthermore corresponds to a concave surface 43 at the perimeter edge of the lower proximal sleeve 20, which edge is intended to abut the convex surface 35 of the supporting plate. Furthermore the supporting plate 32 presents a flat surface facing the prosthetic sleeve 23, whereby this flat surface abuts a lower flat surface of an upper connecting sleeve 21 being affixed to the prosthetic sleeve 23, for instance, by casting. Accordingly, the supporting plate 32 with the pyramid adapter stud 42 and the upper connecting sleeve 21 constitute the upper portion of the adjustment head.

The upper connecting sleeve 21 presents an outer flange 22 casted into the prosthetic sleeve 23. Additionally, the connecting sleeve 21 presents in its lower flat surface a through-hole 33 which is much larger than the diameter of a bolt or a screw 34 which is threaded into a through-hole of the pyramid adapter stud 42 onto the supporting plate 32. Additionally, the screw 34 in the illustrative embodiment is countersinked into an upper washer 36 which, irrespective of the position of the screw 34 in the through-hole 33, principally covers the bore 33. Thus, the upper connecting sleeve 21, the washer 36, the screw 34 passing through and the supporting plate 32 with the pyramid adapter stud 42 constitute the adjustment device in the translatory direction, while the pyramid adapter stud 42, the convex surface 35 of the supporting plate and the lower proximal sleeve 20 with the screws 46 constitute the adjustment device for the angular adjustment of the tube 10.

Figure 3:
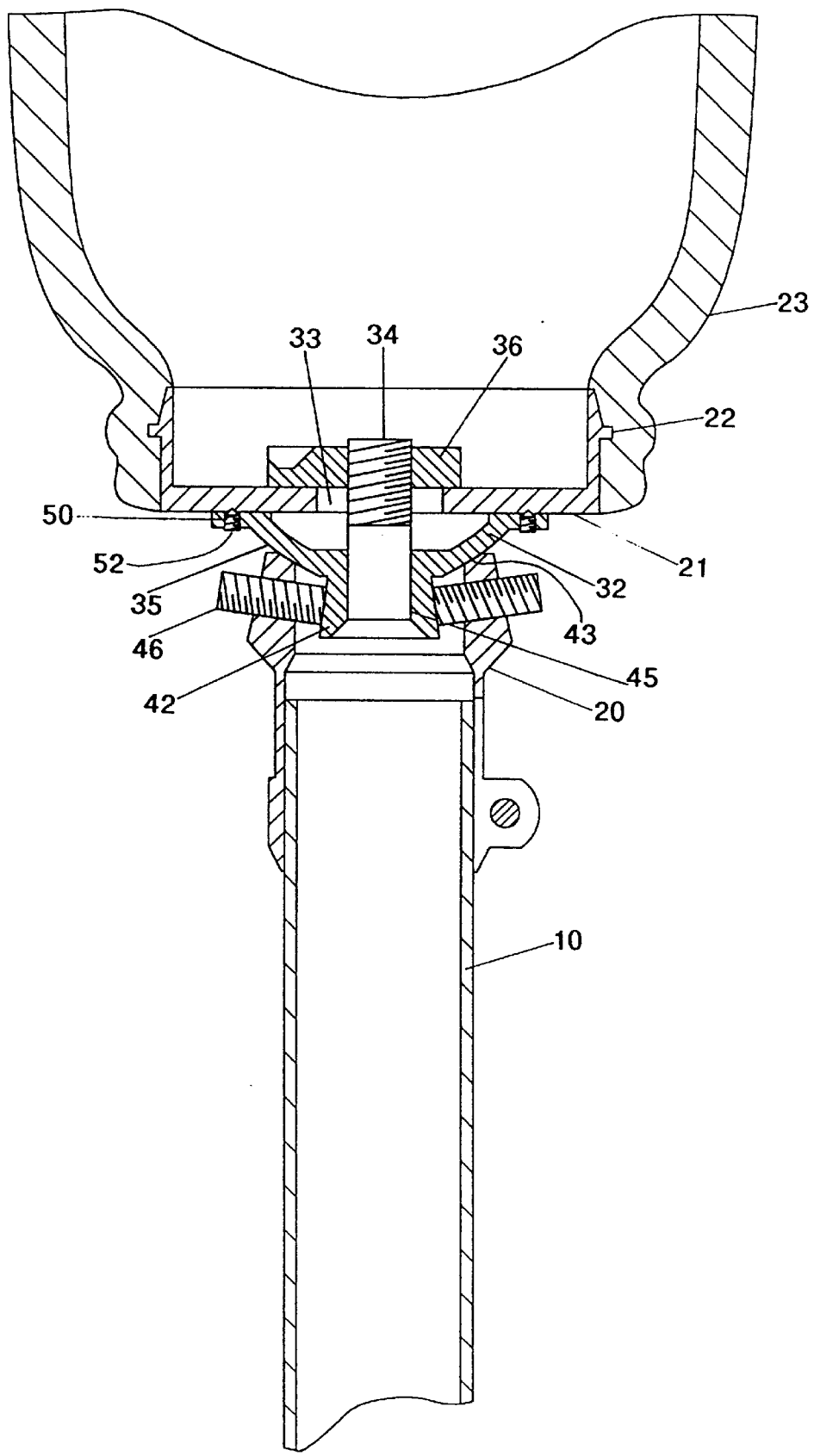
FIG. 3 demonstrates an additional longitudinal cross section of a preferred embodiment according to the present invention.

FIG. 3 shows a preferred embodiment of the present invention. The embodiment according to FIG. 3 differs from the embodiment of FIG. 2 in that the screw or bolt 34 is not threaded in the through-hole of the pyramid adapter stud 42, but the screw or bolt 34 is brought from below through a bore in the pyramid adapter stud 42 and is instead threaded into the washer 36 which preferably is made slightly thicker. Consequently, in the embodiment of FIG. 3 it is possible to adjust the translatory position of the pyramid adapter without removing the prosthetic sleeve 23 from the stump of the leg.

In both embodiments a number of threaded through-holes 50 are additionally arranged at the outer periphery of the supporting plate 32, just outside where the convex surface 35 ends. In the bores 50 locking screws 52 are applied which with a sharp end engage the flat lower surface of the upper connecting sleeve 21 to further mutually lock the supporting plate 32 to the connecting sleeve 21 in the translatory position set.

Due to the construction, according to the present combination of the translatory adjustment device and the angular adjustment device of the present invention, an advantage is obtained compared to, for instance, the disclosed construction according to the Swedish Patent No. SE 454 046, in that the screw for translatory setting will not be subject to direct breaking forces by being angled due to the angular setting of the tube, but this screw all the time maintains a fixed alignment. Furthermore an advantage is achieved in that the tube 10 with the lower proximal sleeve 20 being fixed with the screws 46 may on demand be fully released from the adjustment head without first having to remove the prosthetic sleeve from the stump of the leg. In other words the lower portion of the artificial leg can simply be detached by means of a tool, in this case a socket-head tool, for possible other adjustments without having to take off the prosthetic sleeve.

The forces acting from below in the present combination will primarily be absorbed by the convex surface 35 of the supporting plate, which surface abuts the corresponding concave surface portion 43 of the lower proximal sleeve 20, while the screws 46 constitute only locking of the angular position set.

However, it will be appreciated by those of ordinary skill in the art that the present invention can be embodied in other specific forms without departing from the spirit or essential character thereof. The presently disclosed embodiments are therefore considered in all respects to be illustrative and not restrictive. The scope of the invention is indicated by the appended claims rather than the foregoing description, and all changes which come within the meaning and range of equivalents thereof are intended to be embraced therein.

I claim:

1. A device for attaching an extension element to a leg prosthesis, comprising an adjustment head structured and arranged to be attached to a proximal end of said extension element at a proximal sleeve of said adjustment head and to a leg prosthesis at an upper connecting sleeve of said adjustment head, whereby by means of said adjustment head, in part a setting of an angular position of said extension element relative to an imagined load line, and in part a setting of an translatory position of said extension element relative to said upper connecting sleeve, will be achieved, said adjustment head further comprising a first adjustment means for setting of said translatory position of said extension element, said first adjustment means including a supporting plate having a downwardly facing convex supporting surface and an upwardly facing flat surface facing said upper connecting sleeve, said upper connecting sleeve including a central bore, a first screw extending through said central bore and being translationally displaceable in relation to said upper connecting sleeve;

a second adjustment means for setting of said angular position of said extension element, said second adjustment means comprising an angle adjustment member in the form of a pyramid adapter stud integrated with said convex supporting surface and provided with a through-hole through which said first screw extends, said first screw always maintaining its alignment independent of any angular position of said extension element; and a number of second screws for setting of said angular position of said extension element, said second screws fixed to said proximal sleeve such that inner ends of said second screws are engageable with inclined sides of said pyramid adapter stud when an edge of said proximal sleeve abuts said convex supporting surface of said supporting plate.

2. The device of claim 1 wherein said pyramid adapter stud includes at least three upwardly and inwardly inclined flat sides in relation to a central line of said pyramid adapter stud, and further wherein said second screws comprise at least three screws each of which abut a respective inclined flat side thereby setting said angular position of said extension element and locking said proximal sleeve to said pyramid adapter stud.

3. The device of claim 2 wherein said first screw includes one region which is threaded into said through-hole of said pyramid adapter stud and an opposite region which extends through a washer which in all translatory positions covers said central bore, whereby when said first screw is tightened, the position of said supporting plate and said pyramid adapter stud will be fixed.

4. The device according to claim 3, wherein said supporting plate, at said flat surface includes a number of threaded bores in each of which a threaded screw member may be inserted for an extra locking of said supporting plate in relation to said upper connecting sleeve.

5. The device of claim 2 wherein said first screw includes a first region which bears against said pyramid adapter stud and an opposite second region which is threaded into a washer which in all translatory positions covers said central bore, whereby when said first screw is tightened, the position of said supporting plate and said pyramid adapter stud will be fixed.

6. The device according to claim 5, wherein said supporting plate, at said flat surface includes a number of threaded bores in each of which a threaded screw member may be inserted for an extra locking of said supporting plate in relation to said upper connecting sleeve.

7. An adjustment head, comprising:

an upper portion, comprising:
- a first connecting sleeve having an opening extending therethrough in the direction of a vertical axis and being structured and arranged for attachment to a prosthetic leg;
- a supporting plate having a first bore extending therethrough, a convex surface extending away from said first connecting sleeve and a flat surface facing said first connecting sleeve;
- an adapter stud integrated with and extending away from said convex surface and having a second bore extending therethrough and a plurality of inclined sides, said opening, said first bore and said second bore being in alignment; and
- a first screw extending through said opening, said first bore and said second bore; said first screw, said supporting plate and said adapter stud being movable, relative to said first connecting sleeve, in a radial direction relative to said vertical axis when said first screw is in a loosened mode; and said first screw, said supporting plate and said adapter stud being immovable relative to said first connecting sleeve, and said first screw extending in said direction of said vertical axis, when said first screw is in a tightened mode; and a lower portion, comprising:
  a second connecting sleeve extending from a first end to a second end, said first end comprising a plurality of apertures extending therethrough, each aperture of said plurality of apertures being in alignment with a respective inclined side of said plurality of inclined sides, said second end being structured and arranged for attachment to an elongated element; and a plurality of second screws, each second screw of said plurality of second screws extending into a respective aperture of said plurality of apertures and being moveable for engagement with and disengagement from a respective inclined side, said second connecting sleeve being moveable, relative to said first connecting sleeve, angularly in relation to said vertical axis, when at least one of said second screws is disengaged from a respective inclined side in a first mode, and said second connecting sleeve being angularly immovable relative to said first connecting sleeve when each second screw engages a respective inclined side.

* * * * *